United States Patent [19]

Schenk et al.

[11] Patent Number: 4,745,055

[45] Date of Patent: May 17, 1988

[54] FUSED PROTEIN FOR ENZYME IMMUNOASSAY SYSTEM

[75] Inventors: Dale B. Schenk, Campbell; Sharon K. Spratt, Sunnyvale, both of Calif.

[73] Assignee: California Biotechnology Inc., Mountain View, Calif.

[21] Appl. No.: 868,393

[22] Filed: May 28, 1986

Related U.S. Application Data

[63] Continuation-in-part of Ser. No. 731,853, May 7, 1985, abandoned.

[51] Int. Cl.$^4$ .................... G01N 33/535; C12N 15/00
[52] U.S. Cl. ......................................... 435/7; 435/14; 435/68; 435/70; 435/172.3; 435/188; 435/810; 435/320; 530/350; 935/10; 935/11; 935/29; 935/47
[58] Field of Search .............. 435/7, 14, 68, 70, 172.3, 435/188, 317, 810; 935/10, 11, 29, 47; 530/350

[56] References Cited

U.S. PATENT DOCUMENTS

3,654,090 4/1972 Schuurs .......................... 435/810 X
4,356,270 10/1982 Itakura ........................ 435/172.3 X
4,517,290 5/1985 Iwasa ............................. 435/188 X

OTHER PUBLICATIONS

"Enzyme–Immunoassay", E. T. Maggio, ed., pp. 127–130, CRC Press, Boca Raton, 1980.
Koenen, M. et al., EMBO, 1(4), 509–512 (1982).
Ruther, U. et al., EMBO, 2(10), 1791–1794 (1983).
Ullmann, A.; GENE, 29, 27–31 (1984).
Minton, N. P., GENE, 31, 269–273 (1984).
Casadaban, M. J. et al., J. Bacteriol., 143(2), 971–980 (1980).
Gray, M. R. et al., Proc. Natl. Acad. Sci. USA, 79(21), 6598–6602 (Nov. 1982).
Chemical Abstracts, 102:20786p (1985).
Chemical Abstracts, 103:173415n (1985).
"Methods in Enzymology", vol. 70, Immunochemical Techniques, Part A, H. Van Vunakis et al., eds., Chapt. 28 by E. Engvall, pp. 419–439, Academic Press, New York, 1980.
Andersen, F. A., Biochim. Biophys. Acta (1963) 71: 246.
Arnon, J. Immunol. Meth. (1983) 61:261.
Arnon, et al., Proc. Natl. Acad. Sci. (USA) (1976) 73:2123.
Cravan, G. R., et al., J. Biol. Chem. (1965) 240:2468.
Dzau, V. J., et al., Clin. Exp. Hypertens (1983) 85:1207.
Fuchs, et al., Isr. J. Chem. (1974) 12:681.
Hawgood, S., Biochemistry (1985) 24:184.
Kohler, B., et al., Nature (1975) 256:495.
Lerner, et al., Proc. Natl. Acad. Sci. (USA) (1981) 78:3403.
Lincoln, et al., Rec. Prog. Horm. Res. (1980) 36:1.
Maizel, J. V., Jr., Methods Virology (1971) 5:180.
Maniatis, T., et al., in Molecular Cloning: A Laboratory Manual (1982), Cold Spring Harbor Labs, p. 122.
Maxam, A., et al., Methods in Enzymology (1978) 65:449.
Merrifield, R. B., Biochemistry (1964) 3:1385.
Monoclonal Antibodies (1980) Kennett, R. H. et al., eds., Plenum, 365–367.
Muller, et al., Proc. Natl. Acad. Sci. (USA) (1982) 79:569.
Nakao, K., et al., Biochem. Biophys. Res. Commun. (1984) 124:815.
Shine, J., et al., Nature (1980) 285:456.
Tanaka, I., Biochem. Biophys. Res. Commun. (1984) 124:663.
Ullman, E. F., et al., in Enzyme–Immunoassays (1980), Maggio, E. T., ed., CRC Press, Boca Raton, pp. 105–134.

Primary Examiner—Sidney Marantz
Attorney, Agent, or Firm—Ciotti & Murashige, Irell & Manella

[57] ABSTRACT

A fused protein for use in an enzyme immunoassay system. The protein comprises an enzymatically active β-galactosidase fused, at its C terminus, to an immunologically active peptide. The protein is produced using a plasmid containing a complete β-galactosidase gene fused, at its 3' end, with an oligonucleotide coding for the peptide. The fused protein is designed for use in a solid-phase enzyme immunoassay system, based on immunospecific binding of the fused protein to a solid support, or in a homogeneous enzyme immunoassay system, based on enzyme inhibition resulting from immunospecific binding of an antibody to the protein.

10 Claims, 1 Drawing Sheet

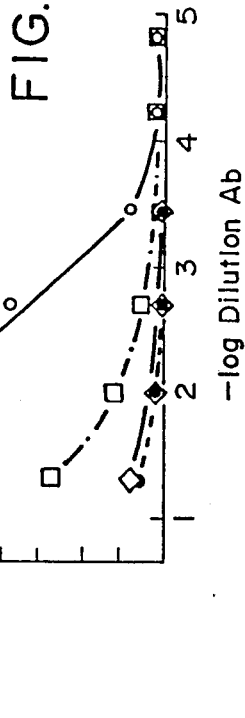
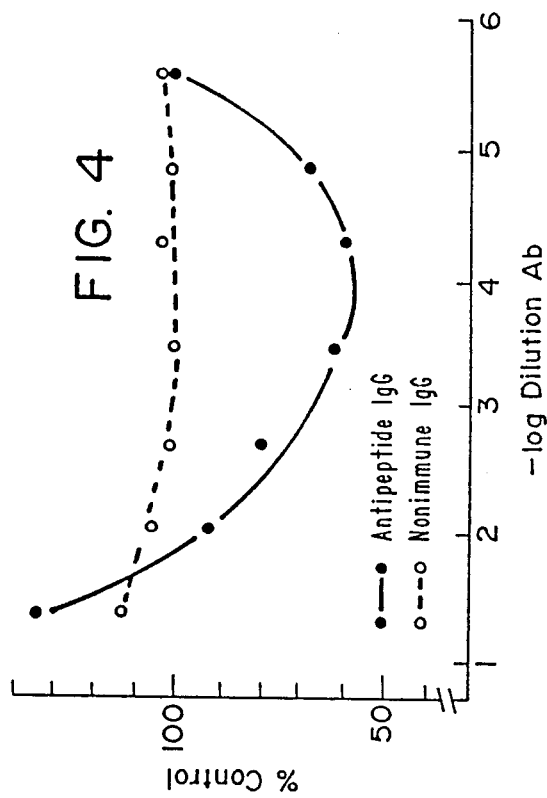
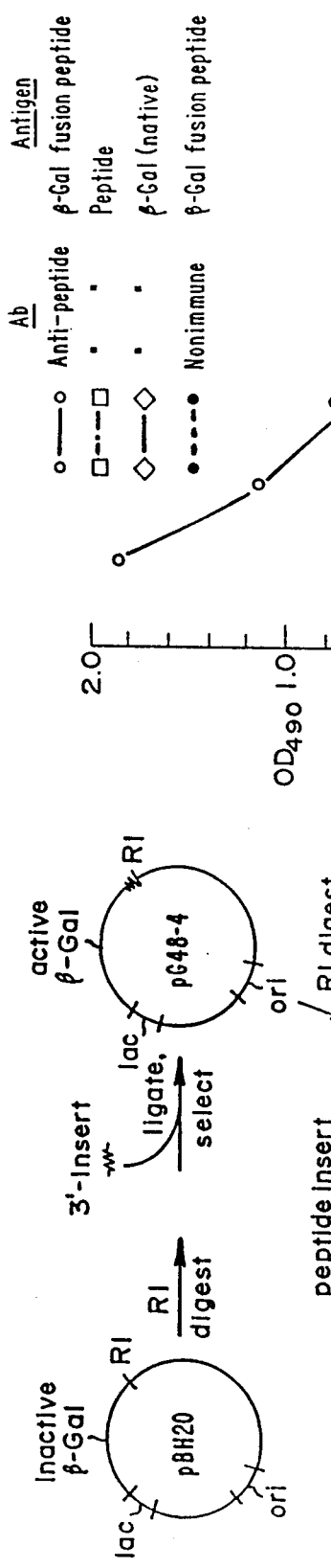
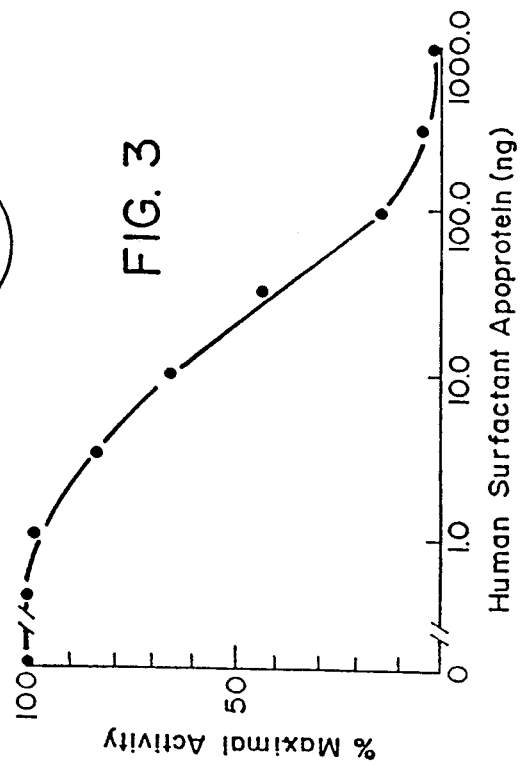

FUSED PROTEIN FOR ENZYME IMMUNOASSAY SYSTEM

CROSS-REFERENCE TO RELATED APPLICATION

This a continuation-in-part of U.S. application Ser. No. 731,853, filed May 7, 1985, now abandoned.

FIELD OF THE INVENTION

The present invention relates to enzyme immunoassay systems and, particularly, to a fused protein for use in determination of a peptide or protein analyte in a solid-phase or homogeneous enzyme immunoassay system.

REFERENCES

The following references are referred to herein by corresponding number:
1. Engvall, E., et al, *J Immunol* (1972), 109: 129.
2. Shine, J., et al, *Nature* (1980), 285: 456.
3. Lincoln, et al, *Rec Prog Horm Res* (1980) 36: 1.
4. Nakao, K., et al, *Biochim Biophys Res Commun* (1984) 124: 815.
5. Dzau, V. J., et al, *Clin Exp Hypertens* (1983) 85: 1207.
6. Tanaka, I., *Biochim Biophys Res Commun* (1984) 124: 663.
7. Arnon, et al, *Proc Natl Acad Sci (USA)* (1976) 73: 2123.
8. Fuchs, et al, *Isr J Chem* (1974) 12: 681.
9. Arnon, *J Immunol Meth* (1983) 61: 261.
10. Anderen, F. A., *Biochim Biophys Acta* (1963) 71: 1246.
11. Lerner, et al, *Proc Natl Acad Sci (USA)* (1981) 78: 3403.
12. Muller, et al, *Proc Natl Acad Sci (USA)* (1982) 79: 569.
13. Merrifield, R. B., *Biochemistry* (1964), 3: 1385.
14. Kohler, B., et al, *Nature* (1975), 256: 495.
15. *Monoclonal Antibodies* (1980), Kennett, T. J., et al, eds, Plenum.
16. Ullman E. F., et al, in "Enzyme-Immunoassays" (1980), Maggio, E. T., ed, CRC Press, Boca Raton, pp. 105–134.
17. Maniatis, T., et al, in *Molecular Cloning: A Laboratory Manual* (1982), Cold Spring Harbor Labs, p. 122.
18. Maxam, A., et al, *Methods in Enzymology* (1978), 65: 449.
19. Maizel, J. V., Jr., *Methods Virology* (1971), 5: 180.
20. Cravan, G. R., et al, *J Biol Chem* (1965), 240: 2468.
21. Hawgood, S., *Biochemistry* (1985) 24: 184.

BACKGROUND OF THE INVENTION

Enzyme-labeled antigens are widely used in solid-phase immunoassays, and have been proposed for use in homogeneous immunoassays. In a solid-phase assay, the enzyme-labeled antigen is designed to complete with an analyte in solution for binding to anti-analyte binding molecules carried on the surface of a solid support. After the initial competitive-inhibition binding reaction, the solid support is washed and assayed for enzyme activity. The amount of enzyme activity associated with the support is inversely proportional to the amount of analyte present in the original assay reaction mixture. This assay system has the advantage of greater sensitivity over solid-phase immunoassay systems employing antigen/fluorophore or antigen/chromophore conjugates. At the same time, the system avoids the problems and expense involved in measuring radionuclides encountered in solid-phase radioimmune assays (RIA), where the analyte-competing antigen is radiolabeled.

In a homogeneous enzyme immunoassay, the enzyme-labeled antigen is designed typically to compete with an analtye for binding to an anti-analyte antibody which is free in the reaction mixture. The relative spatial arrangement of antigen and enzyme is such that antibody binding to the antigen produces a measurable, normally inhibitory effect on the enzyme. Therefore, the presence and/or concentration of analyte in solution can be measured as a change in enzyme activity in the assay mixture.

Heretofore, numerous methods for attaching enzyme labels to antigens to form conjugates for use in enzyme immunoassays have been described (references 1, 2). In general, these methods employ chemical coupling methods, such as periodate oxidation and glutaraldehyde coupling, or cross-linking agents such as o-phenylene dimaleimide, dihydroxysuccinimide, or soluble dicarbodimides. A serious limitation of chemical coupling methods is the difficulty in achieving consistent and reproducible antigen/enzyme coupling in terms of (a) the site(s) of antigen attachment to the enzyme, (b) the number of antigens attached to each enzyme molecules, and (c) the extent of loss of enzymz activity or change in immunological activity of the antigen following coupling. Because of the difficulty in controlling these variables, the manufacturer of the assay kit typically must carry out quality control tests on each batch of enzyme-labeled antigen that is produced. Even with the quality controls, it is difficult to predict how variations in antigen binding to an enzyme will affect the enzyme on storage. Also, a homogeneous-type assay may be quite sensitive to variations in the number of antigens bound to the enzyme and/or their sites of attachment, to an extent that many antigen/enzyme reagent for use in a homogeneous assay canot be produced practically by chemical coupling methods.

U.S. Pat. No. 4,378,428 describes a homogeneous assay system composed of a peptide antigen fused to a small N-terminal fragment of $\beta$-galactosidase antigen antibody, and a complementary C-terminal $\beta$-galactosidase enzyme fragment, both components produced by recombinant DNA techniques. Binding of an anti-antigen antibody to the fused protein interfers with the ability of the N-terminal portion of the enzyme to form an active enzyme complex with a relatively large C-terminal enzyme fragment. This complementary enzyme system is somewhat expensive to manufacture, and is subject to greater assay variations related to enzyme concentration and stability effects than immunoassays systems employing a single enzyme species. Moreover, the system would have limited uses in a solid-phase immunoassay, since the amount of enzyme bound to the solid support could not be assayed directly.

It is therefore an object of the present invention to provide a fused enzyme/peptide protein and methods and systems for producing and using the protein, which overcome above-discussed limitations in prior art enzyme immunoassay reagents.

The invention includes a fused protein reagent for use in an enzyme immunoassay. The protein includes an enzymatically active $\beta$-galactosidase fused, at its C-terminus, to an immunologically active peptide. The active peptide is preferably derived from an immunologically active region of a peptide hormone, a serum protein, or other suitable polypeptide analyte.

The invention further includes a plasmid for use in constructing a fused protein gene. The plasmid contains a complete-sequence β-galactosidase gene which terminates at a selected restriction endonuclease site. In producing the fused protein, a nucleotide coding for the immunologically active peptide is inserted in the plasmid at the selected restriction site, and a transfected host which produces the desired fused protein is identified by the presence of β-galactosidase activity and immunospecific reaction with an anti-peptide antibody.

The fused protein may be used in a solid-phase enzyme immunoassay based on competitive inhibition between an analyte and the fused protein for binding immunospecifically to a solid support. In another embodiment the fused protein forms part of a homogeneous assay system in which antibody binding to the fused protein modulates the protein's enzyme activity.

These and other objects and features of the present invention will be come more fully apparent when the following detailed description of the invention is read in conjunction with the accompanying drawings.

BRIEF DESCRIPTION OF THE DRAWINGS

FIG. 1 illustrates the construction of a plasmid, designated pG48-4, used in constructing fused proteins according to the present invention, and use of this plasmid in constructing a second plasmid, designated pG4817-4, containing a gene capable of expressing a protein with an immunologically active human surfactant apoprotein (HSA) peptide;

FIG. 2 shows levels of specific (open symbols) and non-specific (closed symbols) antisera binding to immobilized β-galactosidase/HSA peptide fused protein (circles), HSA peptide (squares), and native β-galactosidase (triangles), expressed as a function of negative log antiserum dilution factor;

FIG. 3 shows the decrease in enzyme activity associated with a solid support, with increasing amounts of analyte, in a solid-phase competitive inhibition assay; and FIG. 4 shows the change in enzyme activity, as a function of antibody concentration, in a fused protein used in a homogeneous immunoassay.

DETAILED DESCRIPTION OF THE INVENTION

I. Preparation Fused Protein

A. Preparing Plasmid with Complete-Sequence β-Galactosidase Gene

To prepare a fused protein according to the invention, there is first constructed a plasmid containing a β-galactosidase gene which can be expressed in a suitable host as a functionally active enzyme, and which terminates, at its 3' end, at a preferably unique restriction endonuclease site.

Plasmids containing the lactose-controlling elements and a major portion of the β-galactosidase gene from *E. coli* are available, for example, form J. Shine (reference 2). Generally, these plasmids have a unique restriction endonuclease site, such as an EcoRI site, near the 3' end of the β-galactosidase gene, and the gene allows expression of a nearly complete but inactive β-galactosidase enzyme.

The plasmid is modified to have a complete or nearly complete β-galactosidase gene sequence which allows expression of enzymatically active enzyme. This may be done, according to the method of the invention, by constructing a synthetic oligonucleotide which contains the additional 3'-end codons which are needed for expression of a functionally active protein. The oligonucleotide preferably includes, in addition, one or more sticky ends which (a) permit sticky-end ligation of the insert to the endonuclease-cleaved plasmid, and (b) generate a new, preferably unique, restriction endonuclease site at the insert's 3' end, i.e., the 3' end of the elongated gene. The latter condition may require that the sticky end ligation at the insert's 5' end be such as to eliminate the restriction site at which the plasmid was originally cut.

The plasmid and insert ligation products are used to transform a suitable host, such as a β-galactosidase-deficient *E. coli* strain, and transformants are selected typically for antibiotic resistance, provided by the replicating plasmid, and for constitutive β-galactosidase production, as evidenced, for example, by the ability of the colonies to hydrolyze a galactopyranoside substrate which shows an observable color change on enzymatic hydrolysis.

The construction of an exemplary plasmid having a complete-sequence expressible β-galactosidase gene is illustrated in FIG. 1 and detailed in Example I. The pBH20 plasmid used in the construction contains an origin of replication for *E. coli* (ori in FIG. 1), the nucleotide sequence for the lactose-controlling elements (lac), and all but the last 51 nucleotides of the β-galactosidase (β-gal) structural gene. The gene terminates at a unique EcoRI site 17 codons from the 3' end of the complete gene. A plasmid insert containing the 17 missing codons and having EcoRI sticky ends was spliced into the EcoRI site, and the plasmid was used to transform a galactosidase-deficient *E. coli* strain MC1061. Colonies were selected for ampicillin resistance and blue color in the presence of 5-bromo-4-chloro-3-indolyl-β-D-galactopyranoside (X-Gal), evidencing constitutive synthesis of active β-galactosidase. The ligation eliminated the EcoRI site at the 5' side of the plasmid cut and conserved the EcoRI site on the 3' side of the cut, yielding a plasmid with a complete sequence β-galactosidase gene which terminates at a unique EcoRI site.

B. Selecting an Immunogenic Peptide

The fused protein of the invention contains an immunologically active peptide capable of either inducing antibodies which are cross-reactive with the associated analyte, or which reacts immunospecifically with an anti-analyte antibody. The peptide may be an analyte-like peptide, or derived from an immunologically reactive portion of an analyte. Analytes for which the present invention is applicable include, for example, polypeptide hormones, including angiotensin-II, renin, growth hormone, insulin, glucagon, parathyroid hormone, thyroid stimulating hormone, calcitonin, gastrin, leuteinizing hormone, follicle stimulating hormone, human chorionic gonadotropin, LH releasing hormone and atrial natriuretic factor. Detailed amino acid sequences of immunogenic regions of a variety of polypeptide hormones are provided in references 3-6. Example IV below describes the construction of a fused protein whose immunologically active peptide is derived from atrial natriuretic factor.

Another class of polypeptide analytes include large molecular weight proteins (greater than about 10,000 daltons) present in serum or other biological fluids such as amnionic or peritoneal dialysis samples. Proteins in this category include carcinoembryonic antigen, surfactant apoprotein, immunoglobulins, collagen, transferrin, apoprotein-Al, apoprotein-B, fibronectin, α-2-macroglobulin, α-1-antitrypsin, complement C3 and C4, α-fetoprotein, and peptide inhibitors of phospholipase AII. All of these proteins, when present in human serum, are in the concentration range of $10^{-7}$ to $10^{-11}$ M. Examples II and III below detail the construction of a fused protein which includes a 12-amino acid peptide derived from human surfactant apoprotein (HSA). Detailed amino-acid sequence data on immunogenic regions of many of the above proteins is given in references 7-9.

Still another class of polypeptide analytes which are suitable for the present invention include surface immunological proteins of pathogenic organisms, such as viral coat proteins. For a number of viruses, including tobacco mosaic virus, hepatitis B and influenza (references 10-12), detailed studies of the surface coat proteins have indicated a number of immunologically active protein segments from which the fused protein peptide could be derived. Example V below describes the preparation of a fused protein, having, as its immunological peptide, a 29-amino acid segment from influenza virus.

The choice of a suitable immunologically active peptide is based normally on two criteria: (a) predicted antigenicity of the peptide, and (b) cross-reactivity of antibodies toward the peptide and analyte. Generally, highly charged, hydrophilic peptides are antigenic, and therefore a synthetic peptide is preferably derived from a portion of the antigen which is exposed and/or highly charged. When immunologically active regions of a protein are known, these regions will preferably be selected (see, for example, references 3-12).

After selecting a suitable immunologically active peptide for use in the invention, the peptide is first prepared in purified form, according to conventional means, such as by solid-phase synthesis (reference 6). The peptide is used to produce anti-peptide antibodies, for use in selecting plasmid-transfected cells capable of producing the desired fusion protein. The antibodies may also be used in an immunoassay system, to be described below, for determination of the peptide-related analyte.

The anti-peptide antibody may be prepared by conventional means, typically using as an immunogen the peptide conjugated to a protein, such as keyhole limpet hemocyanin. The antibody produced may be used in the form of a whole or partially purified antiserum derived from the challenged animal. Alternatively, peripheral lymphocytes isolated from the challenged animals may be fused with a suitable fusion partner to produce monoclonal antibodies, according to well-known techniques (references 14, 15). The binding activity of the antibody toward the peptide and analyte can be confirmed by standard procedures. The methods detailed in Example III for producing anti-HSA peptide antiserum are generally applicable.

C. Constructing a Fused-Protein Gene

After selecting a suitable analyte-related peptide, and confirming its immunological activity, an oligonucleotide coding for the selected peptide is synthesized for insertion into the above-described plasmid.

The oligonucleotide may be constructed conventionally, for example using an automated DNA synthesizer. Typically, where the oligonucleotide contains more than about 30 bases, the synthetic method involves first constructing two or more shorter, overlapping double-stranded nucleotides, and ligating these together to form the final oligonucleotide. This procedure is illustrated in Examples II, IV, and V below.

The fully synthesized oligonucleotide preferably includes sticky ends corresponding to the sticky ends created when the β-galactosidase gene plasmid is cut at its 3' end. The oligonucleotide is inserted at the 3' end of the above plasmid by standard procedures, which involve cutting the plasmid at its unique restriction site adjacent the 3' end of the complete-sequence β-galactosidase gene, mixing the cut plasmid and peptide-gene insert, ligating, and using the ligation mixture to transform a suitable β-galactosidase-deficient host. Successful transformants are selected on the basis of antibiotic resistance conferred by the plasmid and β-galactosidase activity. The successful transformants are analyzed for correct insert orientation by standard restriction techniques. These methods are illustrated in Examples II, IV, and V.

The selected strain containing the complete-sequence β-galactosidase gene and correct orientation peptide insert is examined for expression of the desired β-galactosidase/peptide fusion protein. Typically, the transformed host, such as E. coli, is lysed by sonication, and the sonicate examined for molecular-weight distribution of lysate proteins, conventionally by SDS polyacrylamide gel electrophoresis (SDS-PAGE).

D. Purification and Characterization of Fused Protein

The fused protein of the invention may be purified by standard techniques, and particularly those applicable to the purification of β-galactosidase (reference 16). Typically, such purification involves an initial ammonium sulfate precipitation, followed successively by ion-exchange and molecular sieve chromatography. The activity of the fused protein-containing fractions is readily followed by the convertion of o-nitrophenol-β-D-galactoside (ONPG) to the colored product. Representative methods for the purification of a β-galactosidase/HSA peptide fused protein are described in Example III.

The presence of an immunologically active peptide in fused protein can be confirmed by standard immunological procedures, such as enzyme-linked immunoadsorbent or Ouchterlony fusion analysis.

II. Enzyme Immunoassays

A. Solid-Phase Assay

In a solid-phase assay, the analyte is allowed to complete with the fused protein for binding a solid support coated with an antibody reactive against both the fused protein and analyte. The antibody-coated support may be prepared by a variety of procedures known in the art for chemically coupling or adsorbing antibody to the surface of a solid support. The surface concentration of antibodies on the solid support is preferably adjusted, in relation to the concentration of fused protein used in the assay, such that the amount of fused protein binding to the solid support is sensitive to the addition of increasing amounts of analyte, within the concentration range of analyte to be tested. With too little antibody carried on the solid support, the support binding sites become saturated at relatively low concentrations of surface-bound fused proteins, and the assay range is correspondingly low. With too much surface-bound antibody, a large amount of analyte will be required to produce appreciable displacement of the fused protein from the solid support and assay sensitivity will be low. In one preferred assay system, the relative concentrations of surface antibody and fused protein are adjusted to produce a level of fused protein binding to the solid support which is about 50% of the maximum amount of the enzyme that can be bound to the support at high surface-antibody and fused protein concentrations. Such preferred levels of antibody and fused protein can be determined by preparing solid supports having a range of different antibody concentrations and incubating each of these with a range of protein concentrations, as detailed in Example VI.

In a typical immunoassay, the solid support is added to a reaction mixture containing the selected concentration of fused protein, and one of a series of different concentrations of the analyte to be determined. The reaction mixture is incubated under conditions which allow equilibration of analyte and fused protein binding to the solid support, typically at room temperature for 30 min. Following the initial binding reaction, the support is separated from the liquid reaction mixture, and the solid support is washed one or more times to remove nonspecifically bound material.

The $\beta$-galactosidase activity associated with the solid support is measured conveniently by placing the support in an assay mixture containing a suitable enzyme substrate. One preferred substrate is ONPG, whose hydrolysis by $\beta$-galactosidase produces a yellow-green color reaction which can be monitored at 495 nm. The solid-phase immunoassay just described is illustrated in Example VI below, which describes a procedure for determination of human surfactant apoprotein. The results of the assay are plotted in FIG. 3 as percent change in $\beta$-galactosidase activity associated with the solid support as a function of the log of the amount of human surfactant apoprotein assayed. As seen, the plot is substantially linear in the analyte range between 1 and 100 nanograms, and within this range, the total enzyme activity associated with this solid support declines more than 80%. The test is sensitive to about 5 nanograms of analyte.

B. Homogeneous Immunoassay

The use of the above fused protein in a homogeneous immunoassay requires that the protein show a measurable enzyme activity effect with antibody binding to the peptide moiety in the protein. The inhibitory effect achievable by antibody binding to the fused protein will depend on such factors as the size of the peptide and the proximity of the immunogenic region of the peptide to the enzyme-active site, the interaction of the peptide and enzyme in the fused protein, the binding affinity of the antibody for the peptide, and the relative concentration of antibody and fused protein. To some extent, these factors can be controlled to optimize the inhibitory effect produced by antibody binding to the fused protein. Generally, the antibody-inhibition effect will be enhanced where the peptide is relatively short, e.g., less than about 20 amino acids, or where the immunologically active region of the peptide is adjacent the enzyme/peptide fusion junction. The other easily controllable factor listed above—the relative concentrations of fused protein and antibody—can be optimized readily by investigating the enzyme activity of the fused protein at increasing antibody concentrations.

The inhibitory effect of antibody binding to a fused protein constructed according to the invention is illustrated in Example VII, which examines the inhibitory effect of anti-HSA antiserum, at a variety of antiserum dilutions, on the $\beta$-galactosidase activity in a $\beta$-galactosidase/HSA peptide fused protein. Percent enzyme inhibition as a function of antiserum dilution is plotted in FIG. 4. The figure shows that the enzymatic activity of the fusion protein can be inhibited significantly (about 40%) by antibody binding, and that optimal relative concentrations of fused protein and antibody are important in achieving a maximal inhibitory effect.

The homogeneous assay may be used for determination either of an anti-peptide antibody analyte, based on direct inhibition of the fused protein enzyme activity by analyte binding, or may be based on competitive inhibition of the analyte for binding to an anti-peptide antibody. In the first, direct-inhibition immunoassay, the fused protein is incubated with serial dilutions of the antibody analyte, under immunoassay reactions conditions like those described above for the solid-phase assay. Following the reaction incubation step, the samples are assayed for $\beta$-galactosidase activity. Example VII illustrates this type of assay for determination for anti-HSA antibody.

In the competitive-inhibition type of homogeneous assay, the fused protein and anti-peptide antibody, preferably at relative concentrations which produce a maximal enzyme inhibition effect, are incubated with serially diluted amounts of the analyte, also under incubation conditions like those described above. Here analyte binding to the antibody in solution decreases the amount of antibody available to the fused protein, producing a reduction in the inhibitory effect seen in the absence of analyte. The data from FIG. 4 indicate that relative concentrations of fused protein and antibody corresponding to an antiserum dilution of 1:10,000 in FIG. 4 would be optimal, since a relatively low concentrations of analyte would be effective to increase enzyme activity measurably above the 60% inhibition level seen in the absence of analyte.

From the foregoing, it can be appreciated how various objects and features of the invention are met. The plasmid of the invention, containing a complete-sequence $\beta$-galactosidase gene which terminates at its 3' end in a unique restriction endonuclease site, permits a fused protein gene to be constructed readily by insertion at the restriction site of an oligonucleotide coding for a selected peptide. The plasmid containing the fused protein gene can be used, in a suitable host, for producing a fused protein having homogeneous and predictable characteristics.

The fused protein, when used in a solid-phase immunoassay system, is capable of producing a highly sensitive linear-range assay for determination of a polypeptide analyte. In another embodiment the fused protein forms part of a homogeneous immunoassay system for use either in the determination of an anti-peptide antibody analyte or for determination of an antigenic polypeptide analyte by competitive inhibition binding to a soluble antibody also forming part of the assay system.

The following examples illustrate various aspects of the invention, but are in no way intended to limit the scope thereof.

Applicable Methods

DNA cleavage is performed by treating with EcoRI under conditions which are generally understood in the art, and the particulars of which are specified by the manufacturer of the commercially available enzyme. See, e.g., New England Biolabs, Product Catalog. In general, about 1 μg of plasmid or DNA sequence is cleaved by one unit of enzyme in about 20 μl of buffer solution; in the examples herein, typically an excess of restriction enzyme is used to insure complete digestion of the DNA substrate. Incubation times of about one hour or two hours at about 37° C. are workable, although variations can be tolerated. After each incubation, protein is removed by extractions with phenol/chloroform, and may be followed by ether extration, and the nucleic acid recovered from aqueous fractions by precipitation with ethanol. If desired, size separation of the cleaved fragments may be performed by polyacrylamide gel or agarose gel electrophoresis using standard techniques.

Ligations are performed typically in 15–30 μl volumes under the following standard conditions and temperatures: 50 mM Tris-Cl, pH 7.5, 10 mM MgCl$_2$, 10 mM DTT, 100 μg/ml BSA, 1 mM ATP, and either 0.01–0.02 (Weiss) units T4 DNA ligase at 0° C. (for "sticky end" ligation) or 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration).

In vector construction employing "vector fragments", the vector fragment is commonly treated with calf intestine phosphatase (CIP) in order to remove the 5' phosphate and prevent religation of the vector. CIP digestions are conducted typically at about pH 9, in approximately 50 mM Tris, in the presence of $Zn^{+2}$ and $Mg^{+2}$, using about 0.01 unit of CIP per μg of vector, depending on size, at 37° C. for about one hour. In order to recover the nucleic acid fragments, the preparation is extracted with phenol/chloroform and ethanol precipitation. Alternatively, religation can be prevented in vectors which have been double-digested by additional restriction enzyme digestion of the unwanted fragments.

The last 17 amino acids of β-galactosidase have the sequence:

```
       1004                    1010                                 1030
Phe—Gln—Leu—Ser—Ala—Gly—Arg—Tyr—His—Tyr—Gln—Leu—Val—Trp—Cys—Gln—Lys
```

A gene fragment coding for these 17 amino acids and having EcoRI sticky ends was prepared from the six overlapping oligonucleotides A–F:

(A). 5'  AATTTCAGCTGAGCGCCGGT                3'

(B). 3'           ACTCGACTCGCGGCCAGCGATG     5'

(C). 5'  CGCTACCATTACCAGTTGGTC               3'

(D). 3'           GTAATGGTCAACCAGACCACA      5'

(E). 5'  TGGTGTCAAAAAG                       3'

(F). 3'           GTTTTTCTTAA                5'

Each oligonucleotide was synthesized on a SAM I automated DNA synthesizer (Biosearch, San Rafael, CA) and purified by preparative gel elctrophoresis. Oligonucleotides (5 μg) were phosphorylated at the 5' end with T4 polynucleotide kinase using the procedure of Maniatis et al (reference 17). Oligonucleotides A and F were not phosphorylated, thereby preventing unwanted polymerization of these fragments at their complementary ends. Phosphorylated and nonphosphorylated oligonucleotides were mixed and annealed at 100° C. for 5 min in a reaction mixture containing 66 mM Tris-HCl, pH 7.5, 6 mM MgCl$_2$ and 0.5 mM ATP. The reaction was cooled to 25° C. for 1 hr followed by the addition of T4 DNA ligase and 10 mM dithiothreitol and an additional 16 hr incubation at 12.5° C. The ligation reaction was analyzed by autoradiography of a sample after polyacrylamide gel electrophoresis. DNA fragments corresponding to the entire insert, as judged by their migration and apparatus molecular weight, were eluted from the gel overnight at 65° C. using DNA elution buffers as described by Maxam (reference 18). The final insert has the sequence:

```
5' AATTTCAGCTGAGCGCCGGTCGCTACCATTACCAGTTGGTCTGGTGTCAAAAAG      3'
3'     AGTCGACTCGCGGCCAGCGATGGTAATGGTCAACCAGACCACAGTTTTTCTTAA 5'
```

EXAMPLE I

Constructing a Plasmid Vector Containing the Entire β-Galactosidase Structural Gene Plasmid pBH20, the construction of which is described in reference 2, was obtained from J. Shine at California Biotechnology Inc. (Mountain View, CA) (reference 2). This plasmid contains the nucleotide sequence for the lactose controlling element and all but the last 51 nucleotides of the β-galactosidase structural gene. The plasmid contains a unique EcoRI site at codon 1004 of the β-galactosidase gene, 17 codons from the 3' end of the gene.

The plasmid was modified by inserting, at the EcoRI site, a synthetic oligonucleotide which provides the remaining 17 codons in the E. coli-β-galactosidase structural gene, and 5' and 3'-end EcoRI sticky ends.

The synthetic β-galactosidase DNA fragment from above was ligated into EcoRI-digested pBH20 according to the Applicable Methods described above. The ligation mix was used to transform the galactosidase-deficient E. coli MC1061, obtained from M Casadaban. Transformants were selected for ampicillin resistance on minimal media plates containing 100 μg/ml ampicillin and 40 μg/ml of 5-bromo-4-chloro-3-indolyl-β-D-galactopyranoside (X-Gal). Colonies constitutive for the synthesis of enzymatically active galactosidase were identified by their blue color (due to the hydrolysis of the X-Gal). Of the 100 colonies examined, 62 were constitutive for β-galactosidase production. Analysis of independent isolates for β-galactosidase activity revealed several with the correctly oriented sequence. One of these clones, designated pG48-4 in FIG. 1, was used for further work.

EXAMPLE II

Construction of a β-Galactosidase/Surfactant Apoprotein Fused Protein

Human surfactant apoprotein (HSA) includes a 12-amino acid antigenic peptide having the following sequence:

Glu-Met-Tyr-Thr-Asp-Gly-Gln-Trp-Asn-Asp-Arg-Asn

To prepare a synthethic oligonucleotide coding for this sequence, and having EcoRI sticky ends, the following oligonucleotides were synthesized:

(A'). 5' AATTCGAGATGTACACCGACGGTC 5'

(B'). 3' GCTCTACATGTGGCTGCCAGTCACCT 3'

(C'). 5' AGTGGAACGACCGTAACTAAG 5'

(D'). 3' TGCTGGCATTGATTCTTAA 3'

The oligonucleotides, were synthesized, purified, isolated, and ligated, as described above. Following ligation, an annealed 48 base pair DNA fragment having the following base sequence was isolated:

5' AATTCGAGATGTACCACCCCGACCGGTCCAGTGGAACCGACCCCGTAACCTAAG 3'
3'     GCCTCCTACCATGTGGCCTGCCCCAGTCCACCCCTTGCCTGGCATTGATTCCTTA 5'

This DNA fragment contains an AATT 5' EcoRI sticky end, the 12 codons corresponding to the 12 amino acids in the surfactant apoprotein peptide segment, a TAA termination codon, and a 3'-end TTAA EcoRI sticky end. The synthetic peptide DNA fragment was ligated to EcoRI-digested pG48-4 under conditions described in the Applicable Methods. The resulting plasmid preparation was transfected into the MC1061 strain of E. coli. The bacteria were grown on minimal media containing ampicillin and X-Gal (40 μg/ml). Transformants with β-galactosidase activity (blue colonies) were selected and examined for the insertion of 48 base pair EcoRI fragment. It can be appreciated that sticky-end ligation of the gene sequence into the EcoRI site of pG48-4 creates the additional two codons GAA and TTG (coding for Asp and Leu, respectively) between the 3' end of the β-galactosidase gene and the 5' end of the 12-codon peptide gene. Those colonies containing the insert in the correct orientation were selected. One such colony, designated pG4817-4 in FIG. 1, was used for further studies.

E. coli strain M1061 transformed with pG4817-4 was grown, lysed by sonication, and examined by SDS-polyacrylamide gel electrophoresis, as described generally in reference 19. The strain transformed with the plasmid pG48-4 -(encoding for native β-galactosidase only) contained a protein with an apparent molecular weight of 116,000 daltons. A β-galactosidase fusion protein produced by the bacterial strain transformed with pG4817-4 migrated with an apparent molecular weight of 118,000 daltons. The control MC1061, lacking a pG48-4 plasmid, did not produce proteins of apparent molecular weight in the range 116,000–118,000 daltons.

EXAMPLE III

Purification and Characterization of β-Galactosidase/HSA Peptide Fusion Protein The β-galactosidase fusion protein from Example III was purified from lysed E. coli cell supernatant according to procedures described by Cravan et al (reference 20). The purification procedure employes the following steps: (1) 50% ammonium sulfate precipitation and dialysis, (2) Sephadex G-200 chromatography, and (3) ion exchange at pH 7.6 with a linear NaCl gradient (0–5%) on DEAE-Sephacel. All procedures were performed at 4° C. and storage of pooled β-galactosidase activity was always in a solution of 50%-saturated ammonium sulfate. The buffer used throughout the purification procedure was 0.1M histidine, 10 mM $MgCl_2$, and 10 mM β-mecaptoethanol. At each step, the presence of the β-galactosidase fusion protein was followed by analyzing an aliquot of each fraction for its ability to convert ONPG to a colored product. Typically, a liter of media yielded 1–2 mg of enzyme with a specific activity of 320–360 units/mg protein (>95% pure).

The presence of an HSA peptide sequence on the β-galactosidase fusions protein was confirmed immunologically. Rabbit antiserum directed against the surfactant apoprotein 13-mer peptide was obtained by the following procedures. The peptide was first synthesized by solid-phase techniques (reference 13). The complete peptide was cleaved from the resin with 32M hydrogen fluoride. The resulting crude peptide was further purified by DEAE-Sephacel chromatography using a combined pH and salt gradient (10 mM ammonium acetate, pH 8.0, to 0.2M ammonium acetate, pH 6.0).

Fractions representing the purified peptide were pooled, lyophilized, resuspended in distilled $H_2O$, and relyophilized. Purified peptide was analyzed by HPLC on a $C_{18}$ column (Bondapak, Waters, Milfred, MA) and showed a single peak. The HSA peptide (5 mg) was conjugated to keyhole limpet hemocyanin (KLH) with carbodiimide using a two-step precedure. Peptide and 5 mg of carbodiimide were incubated in 1 ml of 1 mM HCl for 15 min at 4° C. Nine ml of 1 mM NaOH (25° C.) were added to this mixture followed by 5 mg of KLH. The reaction mixture was shaken overnight at 21° C. and dialyzed against 10 mM $NaH_2PO_4$, 150 mM NaCl (pH 7.4) for 2 days. The HSA peptide/KLH conjugate was emulsified in a 4:6 ratio with complete Freund's adjuvant and 50 μg protein were injected into 5 kg Male Dutch belted rabbits in the footpads. The rabbits were boosted with the same preparation i.m. in their hindlegs 3 weeks later. Ten days later the animals were bled and antiserum was collected and analyzed. Using standard enzyme-linked immunoadsorbent assays (reference 1), the ability of the antipeptide and control antisera to bind to various antigens was investigated.

A plot of antibody binding to (a) the β-galactosidase fusion protein (circles), (b) the surfactant apoprotein peptide alone (squares), (c) native β-galactosidase (diamonds), and (d) binding of β-galactosidase fusion protein to non-immune serum (closed circles) is shown in FIG. 2. As seen, the binding of the fused protein to antiserum (with an apparent titer of 1:1000) was substantially greater than binding of the antiserum to the peptide alone (with an apparent titer of 1:1000). The two controls involving native enzyme binding to antipeptide antiserum and fusion protein binding to non-immune serum both gave low background levels.

EXAMPLE IV

Production of Atrial Natriuretic Factor (ANF) Fused Protein

Human atrial natriuretic factor (ANF) consists of an antigenic peptide containing the following amino acid sequence:

1
Arg—Ser—Ser—Cys—Phe—Gly—Gly—Arg—Met—Asp—Arg—

—Ile—Gly—Ala—Gln—Ser—Gly—Leu—Gly—Cys—Asn—

25
—Ser—Phe—Arg—Tyr

Based on this amino acid sequence, appropriate oligonucleotides having EcoRI sticky ends are synthesized, purified, isolated and ligated as described above. As constructed, this DNA fragment contains a 5' EcoRI sticky end, 25 codons, corresponding to the 25 amino acid sequence of ANF, a termination codon and a 3' EcoRI sticky end. The synthetic peptide fragment is ligated into EcoRI digested pG48-4 and then transfected into the MC1061 strain of E. coli as described above. Colonies expressing the fused protein are selected, grown and the fusion protein purified as described above. Antibodies are prepared against ANF conjugated to hemocyanin as described above for the HSA peptide, and these together with the fusion protein are used in a competitive inhibition test for ANF, as described for HSA in Example VI, or in a homogeneous immunoassay of the type described in Example VII for HSA.

EXAMPLE V

Production of Influenza Hemagglutinin Fused Protein

The hemagglutinin protein contained within the influenza virus contains an antigenic locus (HA1) containing the following amino acid sequence:

297
Phe—Arg—Tyr—Val—Lys—Gln—Lys—Ser—Leu—Met—

—Leu—Ala—Tyr—Gly—Met—Lys—Asn—Val—Phe—Glu—

319
—Asn—Ser—Tyr

Based on this amino acid sequence, appropriate oligonucleotides having EcoRI sticky ends are synthesized, purified, isolated and ligated as described for HSA above. The resulting DNA fragment, having 5' and 3' EcoRI-sticky ends, 23 codons encoding the HA1 C-terminus and a termination codon are ligated into EcoRI digested pG48-4 as described above for HSA. The resulting plasmid is transfected into the MC 1061 strain of E. coli and the fused β-galactoside is purified as described above for the HSA fused protein. Antibodies directed against the HA1 peptide are prepared by synthesizing the peptide by solid phase methods described above and conjugating the peptide to homocyanin for preparation of the immunogen. The HA1 fused protein, together with specific anti-HA1 antibodies is used in either a competitive inhibition test or a homogeneous immunoassay for hemagglutinin.

EXAMPLE VI

Competitive Inhibition Test for HSA

Purified β-galactosidase/HSA peptide fused protein, and rabbit antiserum against HSA peptide were prepared as described in Example III. HSA was obtained in purified form as described in reference 21. Polystyrene microtiter plates were obtained from Flow Laboratories (Mclean, VA).

A competitive inhibition test for determination of HSA was performed by (a) coating a microtiter dish (the solid support) with anti-HSA peptide antibody, (b) reacting the solid support with the analyte and increasing dilutions of the fused protein, (c) washing the solid support to remove nonspecifically unbound material, and (d) measuring the β-galactosidase activity associated with the washed support.

The assay was carried out at a surface concentration of bound antibodies and added fused protein which resulted in 50% of the maximal enzyme activity achievable by binding maximal amounts of fused protein to the solid support. To achieve this 50% enzyme level, various dilutions (1:100, 1:50,000) of anti-HSA peptide antiserum were coated onto the polystyrene surface of a microtiter dish in 0.1M NaHCO$_3$, pH 8.3, for 90 min at 37° C. The wells were washed expensively with wash buffer (25 mN NaPO$_4$, pH 7.4, 150 mM NaCl, and 0.05% (v/v) TWEEN-20). Increasing concentrations of the β-galactosidase/HSA peptide fused protein (0.1–50 ng/ml) were incubated on the plate in 0.1M histidine, pH 7.5, 10 mM MgCl$_2$ for 30 min at 21° C. After washing the plate, the amount of β-galactosidase attached to the plate was determined by the addition of substrate o-nitrophenol-β-D-galactoside (ONPG). The hydrolysis of ONPG was monitored at 495 nm. Fifty percent of the maximal enzyme activity was observed in the plate coated with a 1:5000 dilution of anti-surfactant apoprotein peptide and a 15 ng/ml concentration of the fused protein.

The microtiter dishes, coated with anti-HSA peptide antiserum and washed as described above, were incubated with 15 ng/ml β-galactosidase/HSA peptide fused protein and 50 λ aliquots of HSA in a total volume of 200 λ in 0.1M histidine, pH 7.5, 10 mM MgCl$_2$ for 30 min at 21° C. The total amount of HSA added to the samples ranged from 0.5 to 1000 ng. Following the incubation, the plates were washed with the phosphate buffer/TWEEN solution described above and assayed for associated β-galactosidase activity, as described above. The results obtained, expressed as percent inhibition of enzyme activity, are shown in FIG. 3. As seen the assay is substantially linear in the analyte range of about 1 and 100 nanograms HSA, and gives easily observable enzyme inhibition with as little as 5 ng HSA.

EXAMPLE VII

Inhibition of Fused Protein Enzyme Activity by Anti-HSA Peptide Antibody

This example describes a direct-binding inhibition homogeneous assay for determination of anti-HSA antibody. β-galactosidase/HSA peptide fused protein from Example III (10 ng) in 150 λ was mixed with 150 λ anti-HSA peptide antiserum (Example III) with increasing final dilutions of 1:50 to 1:10$^5$ in histidine buffer. The reaction mixture was incubated for 30 min at 21° C., after which sample aliquots of were assayed for β-galactosidase activity. The results, expressed as percent control β-galactosidase activity (no antibody added) are shown in solid circles in FIG. 4. Also shown in the figure (open circles) is the effect on β-galactosidase activity of increasing dilutions of non-immune IgG. As seen, high levels (less than 1:50 dilutions) of IgG actually increased the enzyme activity of the fused protein, whereas the same amount of non-immune IgG had no effect on fused protein activity. At lower dilutions of IgG (1:100 to 1:100,000), the antipeptide IgG produced a substantial reduction in β-galactosidase activity, a maximal reduction in activity of about 40% being observed at about a 1:1000 to 1:10,000 antiserum dilutions level.

While preferred embodiments and uses of the invention have been described herein, it will be apparent that various changes and modifications may be made without departing from the invention. In particular, it will be appreciated that the basic methods described for constructing a plasmid having a fused protein, isolation and characterization of the resulting fused protein, and use of the fused protein in enzyme immunoassays will apply to virtually any immunlogically active peptide derived from an analyte of interest.

It is claimed:

1. A fused protein for use in a homogeneous enzyme immunoassay, comprising an enzymatically active β-galactosidase fused, at its C terminus, to an immunologically active peptide of human surfactant apoprotein (HSA), and having the property that binding of anti-HSA antibody to said immunologically active peptide inhibits the β-galactosidase activity of said protein.

2. The protein of claim 1, wherein the β-galactosidase is encoded by a complete-sequence, bacterial β-galactosidase gene.

3. The protein of claim 1, wherein the peptide includes the amino acid sequence Glu-Met-Tyr-Thr-Asp-Gly-Gln-Trp-Asn-Asp-Arg-Asn.

4. A plasmid for use in producing in a bacterial host, a fused protein composed of enzymatically active beta-galactosidase fused at its C terminus to an immunologically active peptide of HSA, and having the property that binding of anti-HSA antibody to said protein inhibits its β-galactosidase activity of said protein, comprising:
   (a) an origin or replication which permits plasmid replication in the host,
   (b) lactose-controlling elements, and
   (c) a complete-sequence B-galactosidase gene which is under control of said lactose-controlling elements and which terminates at a unique EcoRI site.

5. A method of producing a fused protein for use in a homogeneous enzyme immunoassay system designed for determination of a protein or peptide analyte, comprising:
   (a) selecting a peptide which is immunologically reactive with an antibody which is cross-reactive with an antigenic region of the analyte;
   (b) providing a nucleotide sequence coding for such peptide;
   (c) constructing a plasmid having a β-galactosidase gene which (1) encodes for enzymatically active β-galactosidase in a suitable host, and (2) terminates at its 3'-end at a selected restriction endonuclease site;
   (d) inserting the peptide-coding sequence into the plasmid at such restriction site; and
   (e) selecting a plasmid transfected host which produces a fused protein which (1) has β-galactosidase activity, (2) is immunologically reactive with an antibody specific against such peptide, and (3) shows increasing inhibition of β-galactosidase activity in response to increasing levels of said antibody added to the fused protein.

6. The method of claim 5, wherein the plasmid gene codes for a complete-sequence bacterial β-galactosidase, and the peptide-coding sequence is inserted at an EcoRI site at the gene's 3' end.

7. The method of claim 5, wherein the peptide is derived from an immunogenic region of human surfactant protein.

8. A homogenous enzyme immunoassay system for determination of a peptide or protein analyte, comprising:
   (a) an anti-analyte antibody effective to bind immunospecifically to said analyte;
   (b) a fused protein composed of an enzymatically active β-galactosidase enzyme fused, at its C terminus, to an immunologically active peptide which is effective to bind said antibody, in proportion to the amount of analyte present in an assay mixture containing the fused protein, antibody, and analyte, to reduce the specific β-galactosidase activity of the fused protein.

9. The system of claim 8, wherein the antibody is present in the assay mixture in an amount which reduces the enzyme activity by at least about 40%.

10. The system of claim 8, wherein the analyte determined is HSA, and wherein the immunologically active peptide has the sequence Glu-Met-Tyr-Thr-Asp-Gly-Gln-Trp-Asn-Asp-Arg-Asn.

* * * * *